(12) United States Patent
Yang

(10) Patent No.: US 10,939,932 B1
(45) Date of Patent: Mar. 9, 2021

(54) EXPANDABLE SURGICAL DEVICES AND METHODS FOR MAKING AND USING THEM

(71) Applicant: Yi Yang, San Francisco, CA (US)

(72) Inventor: Yi Yang, San Francisco, CA (US)

(*) Notice: Subject to any disclaimer, the term of this patent is extended or adjusted under 35 U.S.C. 154(b) by 191 days.

(21) Appl. No.: 16/029,500

(22) Filed: Jul. 6, 2018

Related U.S. Application Data

(62) Division of application No. 14/281,874, filed on May 19, 2014, now Pat. No. 10,016,206.

(60) Provisional application No. 61/824,678, filed on May 17, 2013.

(51) Int. Cl.
*A61B 17/221* (2006.01)

(52) U.S. Cl.
CPC .... *A61B 17/221* (2013.01); *A61B 2017/2212* (2013.01)

(58) Field of Classification Search
CPC .............. A61B 17/221; A61B 17/3205; A61B 17/32056; A61B 17/3207; A61B 17/32075; A61B 17/320725; A61B 2017/320716; A61B 2017/320733; A61B 2017/320741; A61B 2017/2212
See application file for complete search history.

(56) References Cited

U.S. PATENT DOCUMENTS

2008/0058834 A1* 3/2008 Cheng ................ A61B 17/221
606/127

\* cited by examiner

*Primary Examiner* — Melanie R Tyson
(74) *Attorney, Agent, or Firm* — William A. English; Vista IP Law Group LLP

(57) ABSTRACT

A retrieval method for removing clots is provided using a device that includes a shaft carrying an expandable cage. The expandable cage includes a plurality of struts, each strut including proximal and distal ends coupled to non-expandable sections of the shaft distal end and an intermediate region that expands from a collapsed configuration to an expanded configuration. The struts have radial surfaces extending in a radial direction and outer circumferential surfaces in the collapsed configuration, and the intermediate regions of the struts are configured to twist along their lengths when expanded to the expanded configuration, e.g., such that the radial surfaces become oriented substantially circumferentially and the outer surfaces become oriented substantially radially.

13 Claims, 7 Drawing Sheets

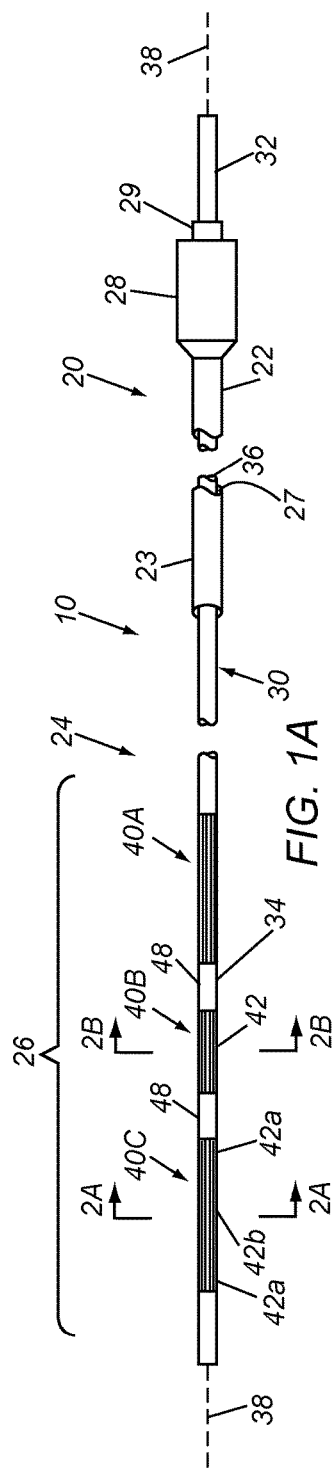
FIG. 1A
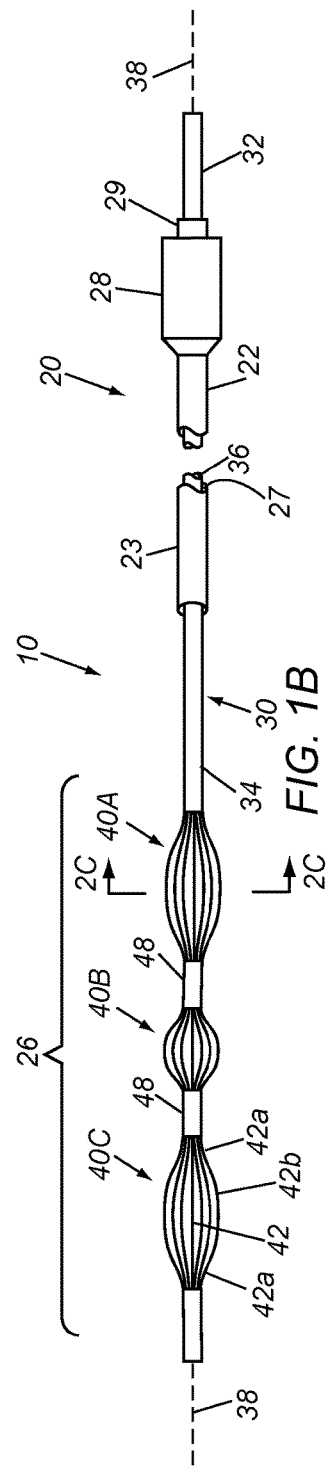
FIG. 1B
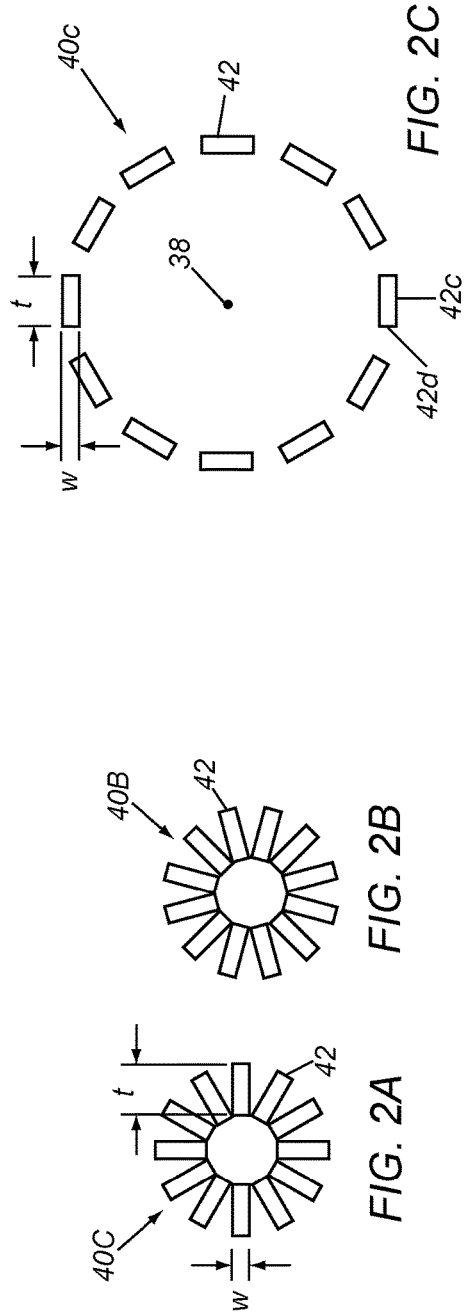
FIG. 2A
FIG. 2B
FIG. 2C

EXPANDABLE SURGICAL DEVICES AND METHODS FOR MAKING AND USING THEM

RELATED APPLICATION DATA

This application is a divisional of application Ser. No. 14/281,874, filed May 19, 2014, and issuing as U.S. Pat. No. 10,016,206, which claims benefit of provisional application Ser. No. 61/824,678, filed May 17, 2013, the entire disclosures of which are expressly incorporated by reference herein.

FIELD OF THE INVENTION

The present invention relates generally to apparatus, systems, and methods for performing medical procedures, and, more particularly, to expandable surgical devices such as vascular clot and emboli retrieving devices, vascular or body cavity snaring devices, and guidewire positioning devices, and to methods for making and using such devices.

BACKGROUND

Several types of devices for removing clots are known. For example, U.S. Pat. No. 8,343,167 to Henson discloses a thrombectomy system and method. U.S. Pat. No. 8,066,757 to Ferrera et al. discloses blood flow restoration and thrombus management methods. U.S. Pat. Nos. 6,511,492; 6,685,722; and U.S. Pat. No. 8,100,935 to Rosenbluth et al. disclose embolectomy catheters and methods for treating stroke and other small vessel thromboembolic disorders. U.S. Pat. Nos. 5,895,398; 6,436,112; 6,485,497; 6,540,935; and U.S. Pat. No. 6,692,509 to Wensel et al. disclose clot capturing coils and methods of using such coils. U.S. Pat. No. 6,679,893 to Tran discloses a grasping device and method. U.S. Pat. No. 5,011,488 to Ginsburg discloses a thrombus extraction system. U.S. Pat. No. 4,706,671 to Weinrib discloses a catheter with a coiled tip. All of these patents are incorporated herein by reference.

Several types of vascular and body cavity snaring devices are known. For example, U.S. Publication No. 2012/0053596 to Gordon discloses a medical snare device. U.S. Publication No. 2008/0275498 to Palmer et al. discloses an embolic basket. U.S. Publication No. 2008/0221587 to Schwartz discloses a two-stage snare-basket medical device. U.S. Publication No. 2004/0059345 to Nakao et al. discloses a medical cauterization snare assembly and associated methodology.

Several types of guidewire positioning devices are known. For example, U.S. Pat. No. 8,328,842 to Brady discloses a filter element with retractable guidewire tip. U.S. Publication No. 2012/0130412 to Duerig et al. discloses a total occlusion guidewire device. U.S. Publication No. 2010/0274270 to Patel et al. discloses a guidewire support catheter. U.S. Publication No. 2008/0086168 to Cahill discloses an implant-catheter attachment mechanism using snare and method of use. U.S. Publication No. 2005/0209559 to Thornton et al. discloses an apparatus and methods for the treatment of chronic total occlusions.

SUMMARY

The present invention is directed to apparatus, systems, and methods for performing medical procedures. More particularly, the present invention is directed to expandable surgical devices such as vascular clot and emboli retrieving devices, vascular or body cavity snaring devices, and guidewire positioning devices, and to methods for making and using such devices.

In accordance with an exemplary embodiment, an expandable surgical device is provided for deployment within a patient's vasculature or other body lumens that includes a tubular body expandable from a collapsed configuration to an expanded configuration, wherein the expandable tubular body includes at least one strut having a cross-sectional width measured in a circumferential direction of the tubular body that is less than a cross-sectional thickness of the strut measured in a radial direction of the tubular body.

In accordance with another embodiment, an expandable surgical device is provided for deployment within a patient's vasculature or other body lumens that includes a tubular body expandable from a collapsed configuration to an expanded configuration, wherein the expandable tubular body includes at least one strut that twists along its length when the tubular body is expanded from the collapsed configuration to the expanded configuration.

In accordance with still another embodiment, a method is provided for retrieving clot, emboli, tissue, or other material from a patient's body that includes inserting an expandable device into the patient's vasculature or other body lumen in a collapsed configuration, expanding the device to an expanded configuration in the body lumen, and retracting the device to thereby capture at least a portion of a clot, emboli, tissue, or other material therein, wherein the device comprises a tubular body expandable from a collapsed configuration to an expanded configuration, the expandable tubular body including at least one strut having a cross-sectional width measured in a circumferential direction of the tubular body that is less than a cross-sectional thickness of the strut measured in a radial direction of the tubular body.

In accordance with yet another embodiment, a method is provided for retrieving clot, emboli, tissue, or other material from a patient's body that includes inserting an expandable device into the patient's vasculature or other body lumen in a collapsed configuration, expanding the device to an expanded configuration in the body lumen, and retracting the device to thereby capture at least a portion of a clot, emboli, tissue, or other material therein, wherein the device comprises a tubular body expandable from a collapsed configuration to an expanded configuration, the expandable tubular body including at least one strut that twists along its length when the tubular body is expanded from the collapsed configuration to the expanded configuration.

In accordance with another embodiment, a device is provided for performing a medical procedure that includes a shaft comprising a proximal end, a distal end sized for introduction into a body lumen, and defining a longitudinal axis therebetween; and an expandable cage carried on the distal end, the expandable cage comprising a plurality of struts, each strut including proximal and distal ends coupled to non-expandable sections of the shaft distal end and an intermediate region that expands from a collapsed configuration to allow the expandable cage to be introduced into a body lumen to an expanded configuration when deployed within a body lumen, the struts having radial surfaces extending in a radial direction relative to the longitudinal axis and outer circumferential surfaces in the collapsed configuration, wherein the intermediate regions of the struts are configured to twist along their length when expanded to the expanded configuration such that the radial surfaces become oriented substantially circumferentially and the outer surfaces become oriented substantially radially.

In accordance with still another embodiment, a device is provided for performing a medical procedure that includes a shaft comprising a proximal end, a distal end sized for introduction into a body lumen, and defining a longitudinal axis therebetween; and an expandable cage carried on the distal end, the expandable cage comprising a plurality of struts, each strut including proximal and distal ends coupled to the shaft distal end and an intermediate region that expands from a collapsed configuration to allow the expandable cage to be introduced into a body lumen to an expanded configuration when deployed within a body lumen, each strut having a radial surface defining a thickness in a radial direction and an outer surface defining a width in a circumferential direction that is smaller than the thickness, and wherein the intermediate region reorients when expanded to the expanded configuration to present the radial surface outwardly.

In accordance with yet another embodiment, a system is provided for removing obstructive material from a body lumen that includes a tubular member comprising a proximal end, a distal end sized for introduction into a body lumen, and a lumen extending between the proximal and distal ends; and an expandable device comprising a shaft comprising proximal and distal ends defining a longitudinal axis therebetween, and an expandable cage carried on the distal end, the expandable cage comprising a plurality of struts, each strut including proximal and distal ends coupled to the shaft distal end and an intermediate region that expands from a collapsed configuration to allow the expandable cage to be introduced into a body lumen through the tubular member lumen to an expanded configuration when deployed within a body lumen, wherein the intermediate regions of the struts are configured to twist along their length when expanded to the expanded configuration to enhance engagement with material captured by the expandable cage.

In accordance with another embodiment, a method is provided for capturing material within a body lumen of a patient's body that includes introducing a distal end of a retrieval device into the body lumen with struts of an expandable cage thereon in a collapsed configuration; positioning the expandable cage adjacent material within the body lumen; expanding the expandable cage to an expanded configuration, thereby causing at least intermediate regions of the struts of the expandable cage to twist along their lengths to enhance engagement with the material within the body lumen; compressing the expandable cage back towards the collapsed configuration to capture the material; and removing the expandable cage in the collapsed configuration from the body lumen.

In accordance with still another embodiment, a method is provided for positioning a guidewire within a body lumen of a patient's body that includes introducing a distal end of an elongate member into the body lumen with struts of an expandable cage thereon in a collapsed configuration; positioning the expandable cage adjacent material within the body lumen; expanding the expandable cage to an expanded configuration, thereby causing at least intermediate regions of the struts of the expandable cage to twist along their lengths within the body lumen, the expandable cage aligning an outlet of a lumen on the distal end at a desired radial location within the body lumen; and advancing a distal end of a guidewire from the outlet into the body lumen into the material.

In accordance with yet another embodiment, a method is provided for positioning a guidewire within a body lumen of a patient's body that includes introducing a distal end of a guidewire into a body lumen from a first direction; introducing a distal end of an elongate member into the body lumen from a second direction with struts of an expandable cage thereon in a collapsed configuration; expanding the expandable cage to an expanded configuration, thereby causing at least intermediate regions of the struts of the expandable cage to twist along their lengths within the body lumen; manipulating the elongate member to capture the distal end of the guidewire in the expanded cage; directing the expandable cage back towards the collapsed configuration to secure the distal end of the guidewire relative to the elongate member; and removing the expandable cage from the body lumen with the expandable cage in the collapsed configuration, thereby directing the distal end of the guidewire in the second direction.

In accordance with another embodiment, a device is provided for performing a medical procedure that includes a shaft comprising a proximal end, a distal end sized for introduction into a body lumen, and defining a longitudinal axis therebetween; an outer expandable cage carried on the distal end comprising a first set of struts; and an inner expandable cage carried on the distal end comprising a second set of struts. The first and second sets of struts may be configured to expand from a collapsed configuration to allow the expandable cages to be introduced into a body lumen to an expanded configuration when the cages are deployed within a body lumen.

In accordance with still another embodiment, a method is provided for capturing material within a body lumen of a patient's body that includes introducing a distal end of a retrieval device into the body lumen with struts of an expandable cage thereon in a collapsed configuration; positioning the expandable cage adjacent material within the body lumen; expanding the expandable cage to an expanded configuration, thereby causing at least first and second sets of struts of the expandable cage to expand within the body lumen, the first set of struts expanding to a first maximum diameter second set of struts expand to a second maximum diameter smaller than the first maximum diameter such that the second set of struts are offset inwardly from the first set of struts; compressing the expandable cage back towards the collapsed configuration to capture the material; and removing the expandable cage in the collapsed configuration from the body lumen.

Other aspects and features of the present invention will become apparent from consideration of the following description taken in conjunction with the accompanying drawings.

BRIEF DESCRIPTION OF THE DRAWINGS

It will be appreciated that the exemplary apparatus shown in the drawings are not necessarily drawn to scale, with emphasis instead being placed on illustrating the various aspects and features of the illustrated embodiments. The drawings illustrate exemplary embodiments, in which:

FIGS. 1A and 1B are side views of an exemplary embodiment of a retrieval device including expandable cages in collapsed and expanded configurations, respectively.

FIGS. 2A and 2B are cross-sectional views of the collapsed cages of FIG. 1A, taken along lines 2A-2A and 2B-2B, respectively.

FIG. 2C is a cross-sectional view of an expanded cage of FIG. 1B, taken along line 2C-2C.

DETAILED DESCRIPTION OF THE EXEMPLARY EMBODIMENTS

Figure 2D:
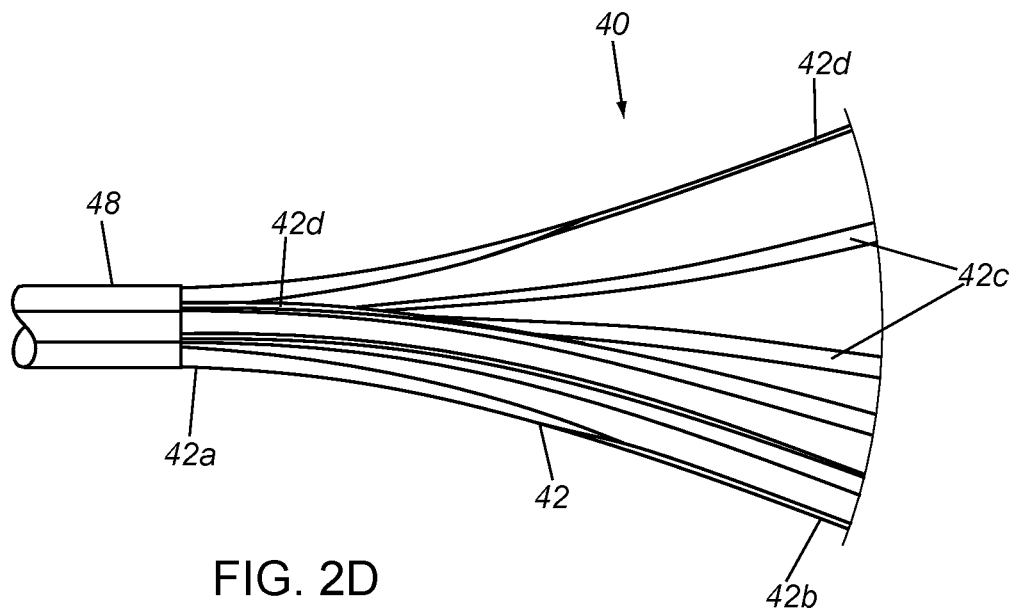
FIG. 2D is a detail of an expanded cage of FIG. 1B.

Turning to the drawings, FIGS. 1A and 1B show an exemplary embodiment of an apparatus 10 for treating a body lumen, e.g., for removing thrombus, clots, objects, debris, and/or other obstructive or unwanted material from within a body lumen, such as a blood vessel, aorto-venous fistula, tubular graft, and the like. In addition or alternative, the apparatus 10 (or any of the other apparatus herein) may be used for other surgical or medical procedures, e.g., that include snaring and/or otherwise manipulating or directing a guidewire, removing a stent or other prosthesis within a body lumen, and the like (not shown), as described elsewhere herein.

Generally, the apparatus 10 includes an access sheath, guide sheath, or other tubular member 20, and a retrieval device 24 including a shaft 30 and one or more expandable cages 40 (e.g., three cages or "web-pods" 40 as shown, or alternatively one, two, or other desired number of cages, not shown). The retrieval device 24 may be introduced into or otherwise positioned in and deployable from the sheath 20, e.g., for removing clot, a prosthesis, or other material from within a body lumen in a patient's body (not shown). The cage(s) 40 may be expandable and compressible between a low-profile, collapsed, or delivery configuration, e.g., as shown in FIG. 1A, and high profile, expanded, or deployed configuration, e.g., as shown in FIG. 1B, and as described further elsewhere herein. Optionally, a system including the apparatus 10 may include one or more additional components, e.g., one or more guidewires, constraints, a source of fluid or vacuum, and the like (not shown).

As shown in FIGS. 1A and 1B, the shaft 30 is an elongate member including a proximal end 32, a distal end 34, and a lumen 36 extending at least partially between the proximal and distal ends 32, 34, thereby defining a longitudinal axis 38 extending therebetween. In one embodiment, the lumen 36 may extend substantially the entire length of the shaft 30, as shown, and the shaft 30 may optionally include one or more regions having different properties, as desired. Alternatively, the lumen 36 may only extend a predetermined distance proximally from the distal end 34, e.g., to provide a rapid-exchange configuration, if desired. The lumen 36 may be sized to slidably receive a guidewire or other rail (not shown), e.g., having an inner diameter of about 0.011-0.040 inch (0.275-1.0 mm) to allow at least the distal portion 26 to be advanced over the guidewire and/or to allow the guidewire to be advanced through and deployed from the lumen 36, e.g., beyond the distal end 34, e.g., as described elsewhere herein.

For example, the shaft 30 may include a substantially rigid or semi-rigid proximal region, e.g., to facilitate advancing and/or otherwise manipulating the distal end 34 within a patient's body from a location outside the body, an intermediate region, and a distal region having the same or variable flexibility, e.g., to facilitate advancement through a patient's vasculature and/or tortuous anatomy without substantial risk of buckling or kinking. In an exemplary embodiment, at least the proximal and intermediate regions may include an inner liner, e.g., including a lubricious inner surface surrounding the lumen 36, an intermediate reinforcement layer, and an outer structural layer (not shown). Alternatively, the entire shaft 30 from the proximal end 32 to the distal end 34 may be formed from a single length of hypotube or other tubular body.

As shown in FIGS. 1A and 1B, the retrieval device 24 may include a distal portion 26 carrying a plurality of expandable cage(s) 40 separated by non-expandable sections 48, which may be formed from a single section of tubular material, e.g., a length of hypotube into which the cage(s) 40 are directly formed. As best seen in FIGS. 1A, 2A, and 2B, a plurality of struts 42 may be provided that define each cage 40, e.g., by creating slots in a hypotube or other tubular body that extend axially along a desired length of the hypotube. In the embodiment shown in FIG. 1A, the struts 42 extend substantially parallel to the longitudinal axis 38 in the collapsed configuration, yet bow radially outwardly away from the central longitudinal axis.

Figure 5A:
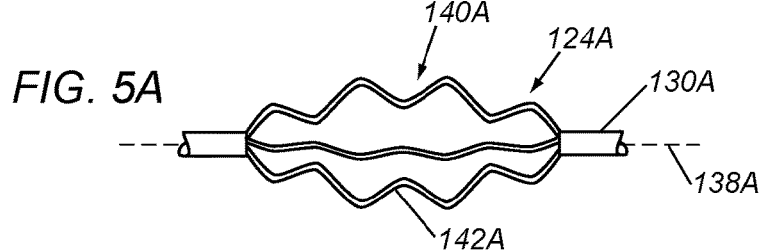
FIGS. 5A-5E are side views of alternative embodiments of expandable cages in expanded configurations that may be included on a retrieval device.
Figure 5B:
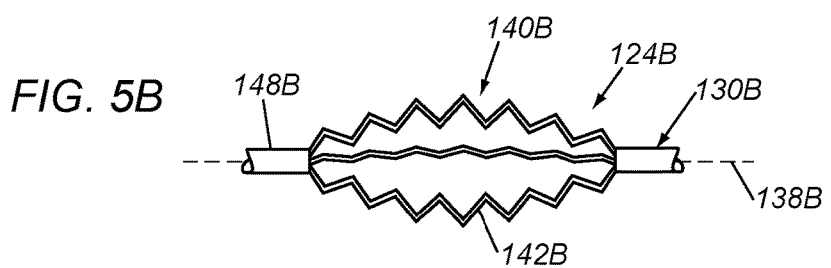
Figure 5C:
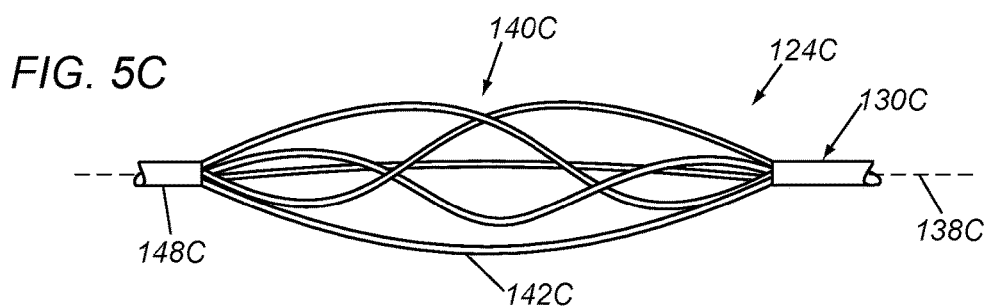
Figure 5D:
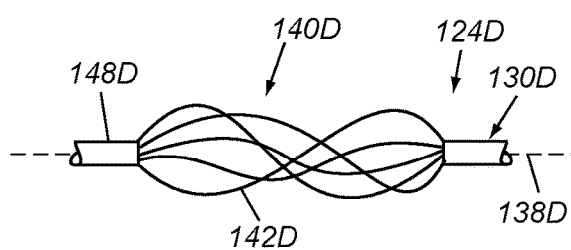
Figure 5E:
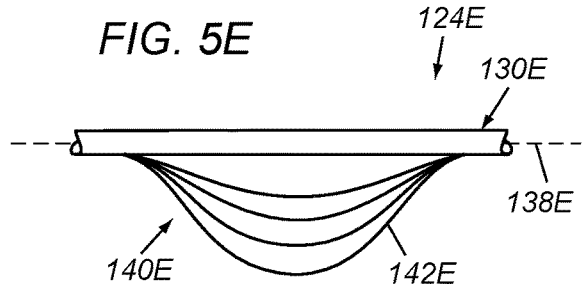

Alternatively, the struts may be formed in other arrangements along the length of the cage(s), e.g., by creating slots or removing material from a tubular body in nonlinear or other patterns, as shown in FIGS. 5A-5E. For example, FIG. 5A shows a retrieval device 124 including a shaft 130 and an expandable cage 140A that includes a plurality of struts 142A formed in a wave pattern wherein the struts 142A extend along the length of the cage 140A in a sinusoidal or other curved pattern. FIG. 5B shows an expandable cage 140B that includes struts 142B that are formed in a zigzag pattern, e.g., including substantially straight elements that are connected together at bends. FIG. 5C shows an expandable cage 140C that includes struts 142C that are formed in an overlapping and/or staggered pattern. FIG. 5D shows an expandable cage 140D that includes struts 142D that extend helically between the ends and around a central longitudinal axis 138D of the cage 140D. FIG. 5E shows an expandable cage 140E that includes struts 142E that extend asymmetrically relative to ends of the cage 140E, e.g., such that the struts 142E are off-centered from a central longitudinal axis 138E.

Returning to FIGS. 1A and 1B (although applicable to other embodiments herein), the cage(s) 40 may be formed from elastic or superelastic materials, e.g., metals, such as stainless steel, Nitinol, and the like, plastics, or composite materials. In an exemplary embodiment, the cage(s) 40 may be formed from a tube with material of the tube cut and/or removed to define the struts 42, e.g., by laser cutting, etching, mechanical cutting, and the like. Alternatively, the cage(s) 40 may be formed from a flat sheet (not shown) also with material cut and/or removed to define the struts 42, e.g., by laser cutting, etching, mechanical cutting, stamping, and the like, and the sheet may be rolled into a tubular shape with edges of the sheet attached together, e.g., by welding, soldering, bonding with adhesive, fusing, and the like.

In an exemplary embodiment, the entire distal portion 26 may be formed from a single hypotube of superelastic material, such as Nitinol, and the struts 42 may be formed directly in the hypotube to provide three cages 40A-40C that are spaced apart from one another along the distal portion 26. Optionally, the struts 42 may be heat treated, e.g., to bias the struts 42 to the expanded configuration yet allow the struts 42 (and consequently the cages 40) to be resiliently compressed into the collapsed configuration for delivery and/or removal. For example, after forming the struts 42, the struts 42 may be positioned in the expanded configuration, whereupon the entire tube may be heated treated, e.g., using known processing methods, to bias the cages 40A-40C to the expanded configuration.

Alternatively, a single cage may be formed from a hypotube or other tubular body, and multiple cages may then be attached to one another to define the distal portion 26 including multiple cages 40, e.g., as shown in FIGS. 1A and 1B. For example, a section of Nitinol hypotube may be formed into each cage 40A-40C, and then the ends may be attached together by sections of tubular material, e.g., metal, plastic, or composite material similar to the other regions of the shaft 30. In a further alternative, ends of each cage 40 may be attached directly to the end of the adjacent cage 40, e.g., by one or more of crimping, bonding with adhesive, fusing, wrapping a collar, wire or other material around the ends, and the like.

Thus, in these embodiments, each cage 40 may be a self-expanding structure, e.g., resiliently compressible radially inwardly to the collapsed configuration yet biased to expand towards the expanded configuration. Alternatively, the cage(s) 40 may be mechanically expanded and collapsed, e.g., using an actuator (not shown) on the proximal end 32 of the shaft 30 coupled to the cage(s) 40, such as an actuating wire coupled to the distal end of each cage 40 that may be directed axially from the proximal end 32 to expand and collapse the cage(s) 40. For example, a guidewire (not shown) over which the device 24 may be advanced may include an enlarged or other positive stop on its distal end (also not shown). In this alternative, the guidewire may be retracted relative to the device 24 to axially compress the cage 40 and cause the struts 42 to bow radially outwardly. To collapse the cage 40, the guidewire may be advanced to disengage the stop and allow the struts 42 to resiliently return to the collapsed configuration. Thus, in this alterative, a capture sheath may not be needed to collapse the cage 40 to introduce the device 24 to a target location.

Optionally, as shown in FIGS. 2A and 2B, the struts of adjacent cages 40 may be offset circumferentially relative to one another. For example, the struts 42 of cage 40C may be aligned along the longitudinal axis 38 with the slots of the adjacent cage 40B, and the struts 42 of cage 40B may be aligned along the longitudinal axis 38 with the slots of the cage 40A. In this manner, the overall cross-sectional area provided by the cages 40A and 40B may be greater than a single cage and/or cages with axially aligned struts (not shown), which may increase the ability of the device 24 to grab and/or remove clot or other material.

Figure 6:
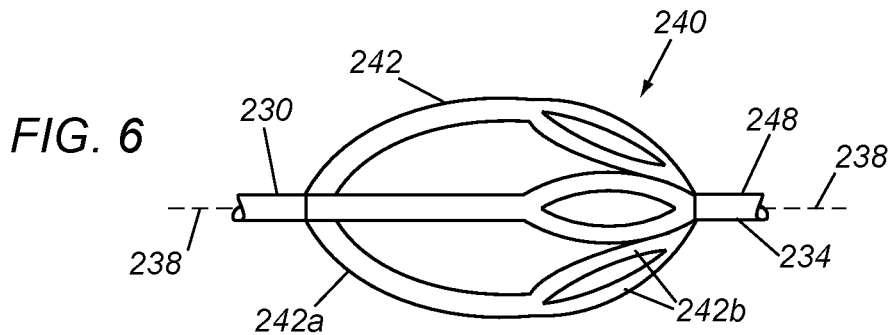
FIG. 6 is a side view of another embodiment of a retrieval device including an expandable cage in an expanded configuration.
Figure 7A:
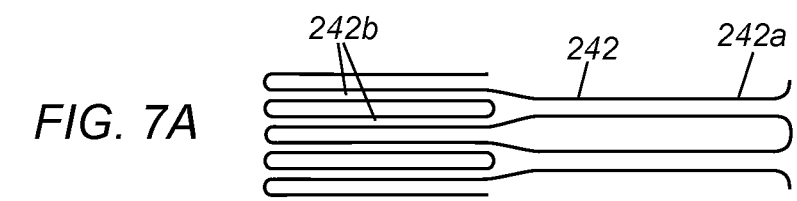
FIGS. 7A and 7B are details showing exemplary struts that may be provided on the expandable cage of FIG. 6.
Figure 7B:

In addition or alternatively, the cage may have different strut densities on different regions of the cage. For example, as shown in FIG. 6, an alternative embodiment of an expandable cage 240 is shown that includes a plurality of struts 242 that provide greater cross-sectional surface area on the distal end of the cage 240 than on the proximal end. As shown, each strut 242 includes a first or proximal end 242a including a single strut segment and a second or distal end 242b that includes a pair of strut segments. FIG. 7A shows a detail of representative struts 242 including the single proximal segment 242a and a pair of distal segments 242b that are symmetrical relative to the longitudinal axis of the proximal segment 242a. FIG. 7B shows a detail of alternative struts 242' that include a pair of distal segments 242b' that are offset or asymmetrical relative to the proximal segment 242a.' The higher surface area provided by the distal segments 242b, 242b' may enhance capturing clot or other material within the cage 240, e.g., enhancing the ability to pull the material proximally and/or reducing the risk of the material escaping beyond the distal end of the cage 240.

In addition or alternatively, the cages 40 may be biased and/or configured to expand to different diameters. For example, as shown in FIG. 1B, the central cage 40B may be biased to expand to a smaller outer diameter than the proximal and distal cages 40A, 40C. In addition or alternatively, the different cages 40 may have different length struts 42, e.g., with the central cage 40B having shorter struts 42 than the proximal and distal cages 40A, 40C, which may limit the expanded outer diameter of the central cage 40B relative to the others.

Figure 8A:
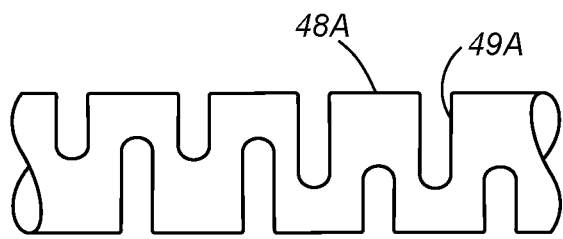
FIGS. 8A and 8B are details showing exemplary strut patterns that may be provided on non-expandable sections of a retrieval device.
Figure 8B:
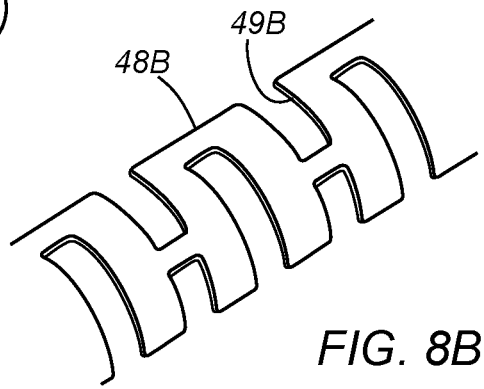

In another option, non-expandable sections between the cages 40 (or adjacent a proximal end or a distal end of a single cage) may include one or more features to enhance flexibility of the sections. For example, FIGS. 8A and 8B show exemplary embodiments of non-expandable sections 48A, 48B that may be provided between the adjacent cages 40 shown in FIGS. 1A and 1B. As shown, the non-expandable sections 48A, 48B include circumferential slots 49A, 49B that extend partially around the periphery of the sections 48A, 48B, which may enhance flexibility, torquability, and/or trackability of the distal portion 26, e.g., during introduction and/or deployment within a body lumen. For example, adjacent slots 49A, 49B may be staggered or otherwise offset from one another such that the sections 48A, 48B may be resiliently bent or curved in any desired direction, yet may resiliently return towards a substantially straight configuration.

In yet another option, to maintain a self-expanding cage (or multiple cages) 40 in the collapsed configuration, e.g., during introduction through or before deployment from the sheath 20, a tubular sleeve or other constraint (not shown) may disposed around at least the distal portion 26 of the shaft 42. For example, the constraint may be an elongate tubular body (not shown) including proximal and distal ends and a lumen extending therebetween that is sized to receive the shaft 30 and cage(s) 40 with the cage(s) 40 in the collapsed configuration. Alternatively, other removable constraints may be provided around the cage(s) 40 to maintain the cage(s) 40 in the collapsed configuration until it is desired to deploy and expand the cage(s) 40 within a body lumen, e.g., one or more removable wires wound around the cage(s) 40, a tear-away sleeve, and the like (not shown). During use, the retrieval device 24 and constraint may be introduced into the sheath 20 already positioned within a patient's body, e.g., as described further elsewhere herein.

Alternatively, the sheath 20 may include a lumen 27 sized to slidably receive the shaft 30 with the cages 40 in the collapsed configuration. For example, the sheath 20 may be an elongate tubular body including a proximal end 22, a distal end 23 sized for introduction into a body lumen, and a lumen 27 extending therebetween. The sheath 20 may be configured for percutaneous placement within a body lumen, e.g., including a tapered, rounded, or otherwise substantially atraumatic tip to facilitate advancement into and/or along body lumens within a patient's body.

The sheath 20 may have a substantially uniform construction along its length, or alternatively, the construction may be varied. For example, the proximal end 22 of the sheath 20 may be substantially rigid or semi-rigid to facilitate advancement of the distal end 24 by pushing or otherwise manipulating the proximal end 22. In addition or alternatively, the distal end 24 may be flexible, e.g., to facilitate bending and/or advancement through tortuous anatomy without substantial risk of kinking or buckling. In exemplary embodiments, the sheath 20 may be formed from materials such as a metal, plastic, or composite materials. The sheath 20 may have a length between about fifty and three hundred fifty centimeters (50-350 cm) and an outer diameter between about one and three millimeters (1.0-3.0 mm), and the lumen 24 may have a diameter between about 0.5-2.75 millimeters.

Optionally, the sheath 20 may include a handle or hub 28 on the proximal end 22, which may be shaped to facilitate holding or manipulating the sheath 20. In addition, the handle 28 may include a port 29 communicating with the lumen 27, e.g., including one or more hemostatic seals (not shown) that prevents fluid from escaping from the lumen 27 while accommodating introduction of the retrieval device 24, a guidewire, and/or other instrument (not shown) into the lumen 27. Optionally, the handle 29 may include one or more additional ports, e.g., a side port (not shown) for coupling a source of fluid for infusing fluid into the lumen 27 and/or a source of vacuum for aspirating material from the lumen 27, e.g., around the retrieval device 24.

As best seen in FIGS. 2A-2D, each cage 40 may include a plurality of struts 42, e.g., between three and twenty four (3-24) struts, such as the twelve (12) struts shown. The struts 42 include first and second ends 42a fixed to non-expandable regions 48 of the distal portion 26, e.g., extending between the adjacent cages 40, and an intermediate region 42b configured to expand radially outwardly away from the central axis 38 into a desired shape, e.g., an elongated spheroid shape, a substantially spherical shape, and the like. As shown in FIGS. 2A and B, in the collapsed configuration, each strut has a thickness "t" in the radial direction (relative to the central axis 38) and a maximum width "w" in the circumference direction (i.e., around the perimeter of the cage 40), with the width smaller than the thickness. Optionally, the width of each strut 42 may taper from the outer surface (i.e., the maximum width) to the inner surface (i.e., the minimum width corresponding to the diameter and thickness of the tubular body from which the struts 42 are formed) or, alternatively, the struts 42 may have substantially uniform width, e.g., as shown in FIG. 2C. In exemplary embodiments, the thickness may be between about 0.1-0.4 millimeter, e.g., 0.155 mm, and the maximum width may be between about 0.05-0.2 millimeter, e.g., about 0.08 mm at the outermost region, such that the ratio of the thickness to the maximum width is greater than one (>1:1), e.g., between about 1.5:1 and 3:1.

Given the cross-section of the struts 42, the intermediate regions 42b may reorient when the cage 40 is expanded from the collapsed configuration to the expanded configuration. For example, if an elastic or superelastic cage 40 is deployed within a body lumen, the struts 42 may resiliently open towards the expanded configuration and the intermediate regions 42b at least partially rotate or twist, e.g., about ninety degrees (90°) such that at least a portion of the thickness surfaces 42c reorient from extending radially to become oriented substantially circumferentially and conversely at least a portion of the width surfaces 42d reorient from extending circumferentially to become oriented radially, e.g., as shown in FIGS. 2C and 2D. For example, this reorientation may provide a lower energy state for the struts 42 as they expanded due to the relatively narrow width of the struts 42 compared to their thickness.

This twisting motion occurring as the struts 42 move from the collapsed configuration to the expanded configuration may provide one or more benefits. For example, the twisting action may cut through and/or agitate clot material during initial expansion of the cage(s) 40. In addition, when the expanded struts 42 contact the wall of a body lumen, the rotated struts 42 may be less traumatic due to their wider surface area and/or may increase the contact surfaces of the cage 40 that contact the clot, allowing for improved clot engagement and/or removal compared to conventional clot retrievers.

For example, a conventional retrieval device formed from a one inch long, 0.027 inch outer diameter section of tubing has a maximum potential surface area of around 0.17 square inch, assuming that all of the material is retained in the cutting process and expands radially outwardly. By comparison, an expandable cage 40, such as that shown in FIGS. 1A and 1B, formed from a one inch, 0.027 inch outer diameter section of tubing having a wall thickness of 0.006 inch has a maximum potential surface area of 0.34 square inch (i.e., about twice as much as could be achieved with a standard cut piece of tubing), assuming that all of the material is retained in the cutting process and the maximum number of 0.003 inch width struts 42 are cut into cage 40 and the struts 42 all rotate ninety degrees. Note that the maximum potential surface area is directly proportional to the ratio between strut thickness and width, e.g., a 2:1 ratio as described above may result in a two-fold increase in potential surface area compared to a normal straight tube. Similarly, a 3:1 ratio may result in a three-fold increase in potential surface area.

Figure 3:
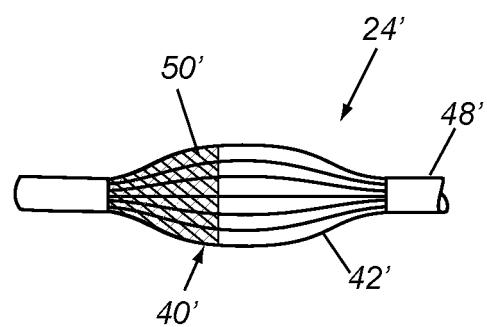
FIG. 3 is a side view of another embodiment of a retrieval device including a filter mesh carried on an expandable cage.

Optionally, as shown in FIG. 3, a retrieval device 24' (or any of the other embodiments herein) may include a mesh or other filter material on one or more cages, e.g., on a single cage 40'. As shown, filter mesh 50' may be provided on the cage 40,' e.g., attached to the struts 42' (or alternatively on the distal cage 40A of the multiple cage device 24 of FIGS. 1A and 1B). As shown in FIG. 3, the mesh 50' may be provided on a distal half of the cage 40', e.g., such that the mesh 50' is expanded substantially across a body lumen within which the cage 40' is expanded such that fluid or materials flowing along the body lumen pass through the pores of the mesh 50'. The pores of the mesh 50' may have a predetermined pore size to capture embolic material above a desired size, e.g., about 100 microns, released during use of the retrieval device 24'. Alternatively, a solid plastic coating or material may be provided instead of the mesh 50' to prevent material from escaping beyond the cage 40.'

Figure 4:
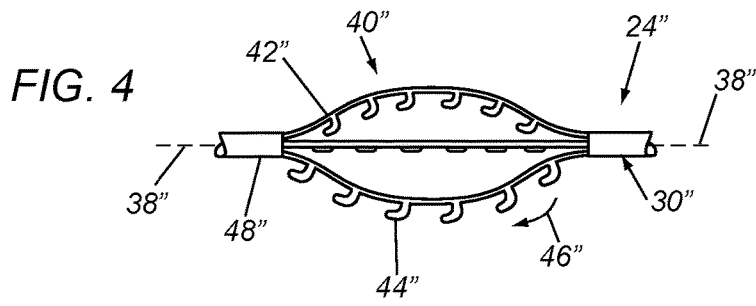
FIG. 4 is a side view of another embodiment of a retrieval device including an expandable cage in an expanded configuration that includes engagement features.

In addition or alternatively, the cage(s) 40 may include one or more features to enhance capturing and/or otherwise engaging a target object to be retrieved using the apparatus 10. For example, as shown in FIG. 4, a cage 40" of a retrieval device 24" is shown in which each strut 42" includes a plurality of hooks or other engagement elements 44" that may be rotated when the struts 42" twist or rotate during expansion. In the embodiment shown, when the cage 40" is in the collapsed configuration, the hooks 44" may be oriented circumferentially, e.g., such that the hooks 44" extending from one strut 42" may be oriented towards the adjacent strut 42." As indicated by arrows 46," the hooks 44" may be rotated as the struts 42" twist during expansion, thereby pulling clot or other material captured by the cage 40" radially inwardly and/or otherwise secured the material to the cage 40," which may facilitate removal, as described elsewhere herein.

Generally, the hooks 44" may be generally "L" or C" shaped members or simply tabs (not shown) extending circumferentially from the thickness surfaces of the struts 42." In the example shown, a plurality of hooks 44" may be spaced apart from one another along the length of each strut 42." Alternatively, in the collapsed configuration, the hooks 44" may extend radially outwardly, e.g., from the width surface of the struts 142" (not shown), and may rotate substantially ninety degrees (90°) toward the interior of the cage 40," e.g., again to enhance engaging clot or other material, as described further elsewhere herein. The hooks 44" may be integrally formed from a hypotube, e.g., when the struts 42" are formed, or may be formed separately and attached to the respective struts 42," e.g., by one or more of bonding with adhesive, welding, soldering, cooperating connectors (not shown), and the like.

Optionally, in any of the embodiments herein, a hydrophilic coating may be applied along the entire length or different regions of the retrieval device 24, e.g., to the inner surface defining the lumen 36 of the shaft 30 and/or to outer surfaces of the shaft 40, e.g., to improve device trackability and/or maneuverability.

In addition or alternatively, in any of the embodiments herein, one or more markers (not shown) may be provided on the retrieval device. For example, radiopaque markers, echogenic markers, and the like may be provided on desired locations of the distal portion 26, e.g., on the non-expandable sections 48, on one or more of the struts 42, and the like, to facilitate monitoring the location and/or orientation of the cage(s) 40 before or after deployment using external imaging, such as fluoroscopy, ultrasound, and the like.

Figure 13A:
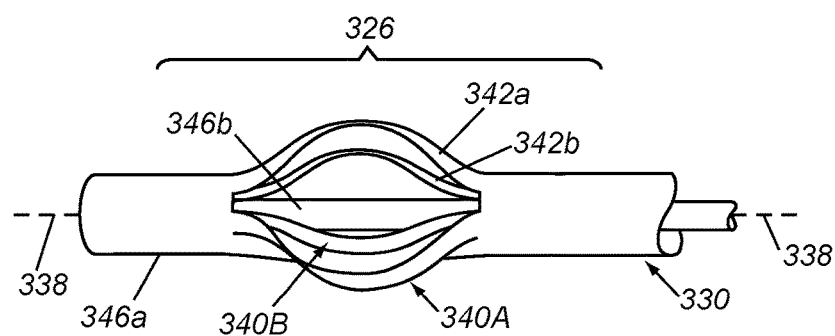
FIGS. 13A and 13B are side views of exemplary embodiments of retrieval devices including alternative embodiments of expandable cages that include inner and outer sets of struts.

Turning to FIG. 13A, another exemplary embodiment of a retrieval device 324 is shown that includes an elongate shaft 330 carrying an expandable cage 340 including a plurality of struts 342, which may be generally constructed similar to other embodiments herein. Optionally, the struts 342 may have a circumferential width that is the same or greater than their thickness unlike the previous embodiments herein. Unlike the previous embodiments, the retrieval device 324 includes an outer cage 340a including an outer set of struts 342a and an inner cage 340b including an inner set of struts 342b that are expandable to a smaller maximum diameter than the outer set of struts 342a.

For example, as shown, the distal portion 326 includes an outer tube 346a having the outer struts 342a formed therein and an inner tube 346b having the inner struts 342b formed therein. The outer and inner tubes 346a, 346b may both extend from the distal portion 326 proximally to a proximal end of the retrieval device 324, e.g., thereby defining the shaft 330. In this embodiment, the tubes 346 may be fixed relative to one another, may be slidable axially relative to one another and/or may be rotatable around a central axis of the tubes 346 relative to one another. Alternatively, only one of the tubes 346 may extend from the distal portion 326 to the proximal end of the shaft 330. In another alternative, both tubes 346 may be provided on the distal end 334 of a separately constructed shaft 330.

The outer and inner struts 342 may be expandable to the same or different maximum outer diameters. For example, the outer struts 342a may be biased to expand to a first outer diameter and the inner struts 342b may be biased to expand to a second outer diameter that is smaller than the first outer diameter.

The outer and inner tubes 346a, 346b may be attached or substantially fixed relative to one another, e.g., to aligned the inner struts 342b within the outer struts 342a. As shown, the inner struts 342b may be aligned within respective outer struts 342a, e.g., such that the outer struts 342a overlie the inner struts 342b in the collapsed configuration (not shown). Both sets of struts 342 may extend substantially parallel to a longitudinal axis 338 of the shaft 330 in the collapsed configuration. Alternatively, the struts 342 may extend helically or in other patterns, similar to other embodiments, with the outer struts 342a overlying the inner struts 342b. Alternatively, the outer and inner struts 342a, 342b may not be aligned with one another. For example, the outer struts 342a may be circumferentially offset from the inner struts 342b.

Figure 13B:
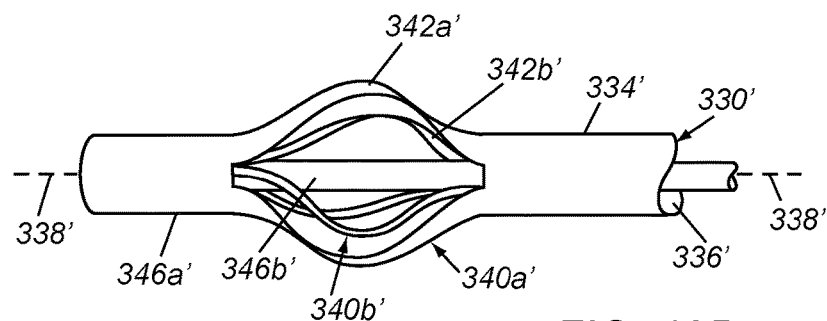

In a further alternative, shown in FIG. 13B, first or proximal ends of the inner struts 342b' may be circumferentially aligned with the outer struts 342a' and second or distal ends of the inner struts 342b' may be circumferentially offset from the outer struts 342a.' For example, in the collapsed configuration, the outer struts 342a' may extend substantially parallel to the longitudinal axis 338' and the inner struts 342b' may extend helically relative to the longitudinal axis 338.' Optionally, in this alternative, one or more regions of the inner struts 342b' may be attached to respective regions of the outer struts 342a.' For example, as shown in FIG. 13B, first or proximal ends of the inner struts 342b' may be attached to first or proximal ends of the outer struts 342a' at one or more locations, e.g., to couple the proximal ends together and provide a first cross-sectional area defined by the struts 342.'

The distal ends of the struts 342 may be offset such that distal ends of the inner struts 342b' are disposed between adjacent distal ends of the outer struts 342a, or the distal ends of the inner struts 342b' may be aligned with distal ends of circumferentially offset outer struts 342a.' Thus, in this alternative, the second or distal end of the cage 340' may have a second cross-section area defined by the struts 342' that is more dense than the first or proximal end, which may increase the ability of the cage 340' to engage clot and/or reduce the risk of material being released beyond the distal end.

The outer and inner struts 342 may be constructed of similar materials or different materials. For example, the struts 342b of the inner cage 340b may be more rigid than the outer struts 342a, e.g., to enhance the inner cage 340b engaging clot or other material to be removed and/or such that the outer struts 342a are softer and/or more flexible, e.g., to reduce the risk of tissue damage when the cages 340 are expanded within a blood vessel.

Figure 9A:
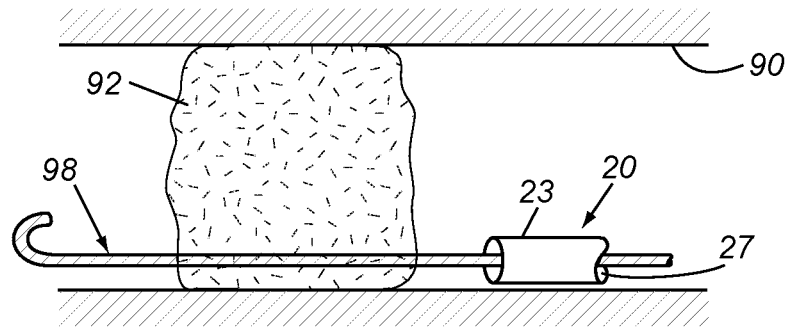
FIGS. 9A-9C are cross-sectional views of a body lumen within a patient's body showing a method for capturing clot within the body lumen.
Figure 9B:
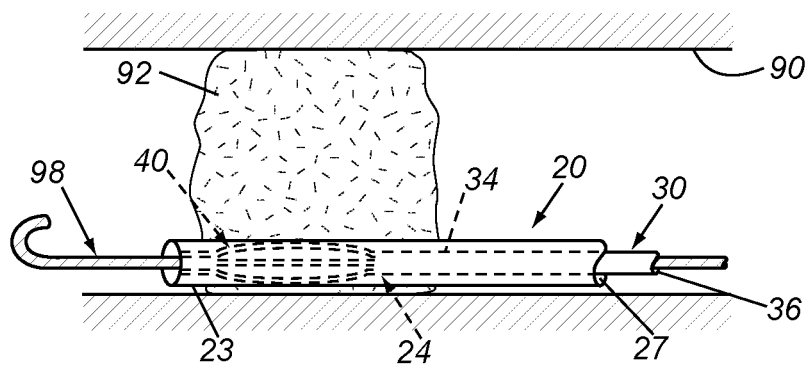
Figure 9C:
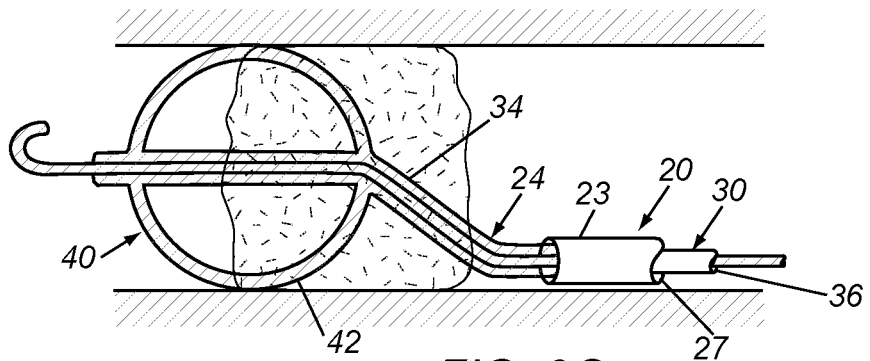
Figure 10A:
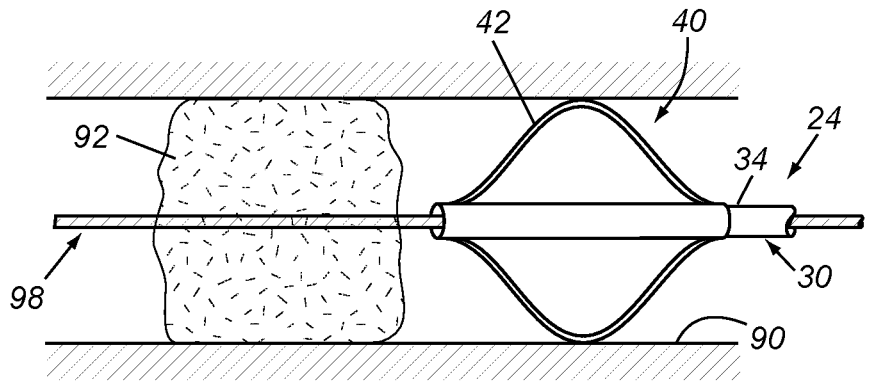
FIGS. 10A and 10B are cross-sectional views of a body lumen within a patient's body showing methods for positioning a guidewire relative to clot within the body lumen.
Figure 10B:
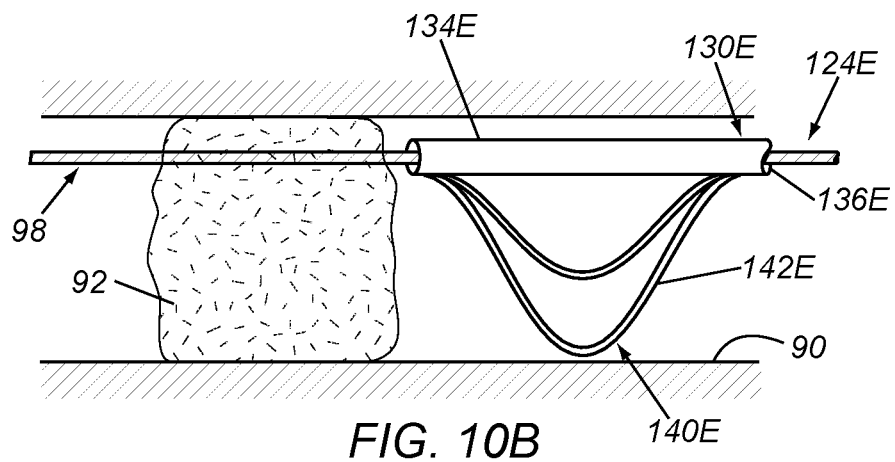
Figure 11:
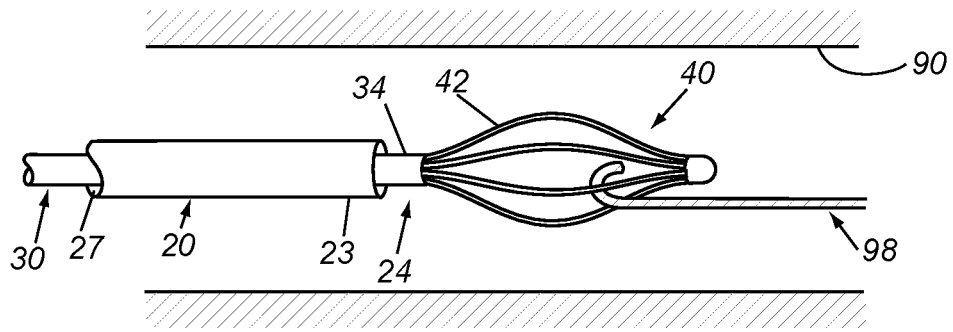
FIG. 11 is a cross-sectional view of a body lumen within a patient's body showing a method for snaring a guidewire within the body lumen.
Figure 12A:
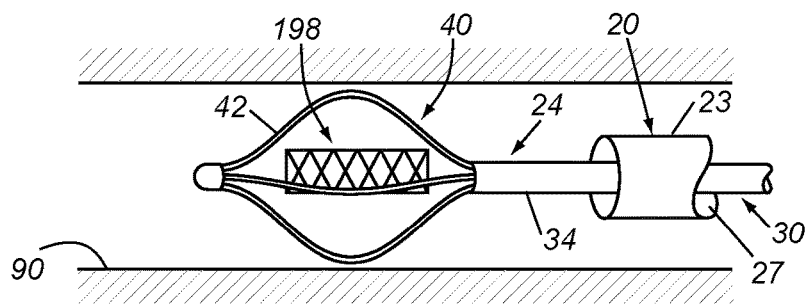
FIGS. 12A and 12B are cross-sectional views of a body lumen within a patient's body showing a method for capturing a prosthesis within the body lumen.
Figure 12B:
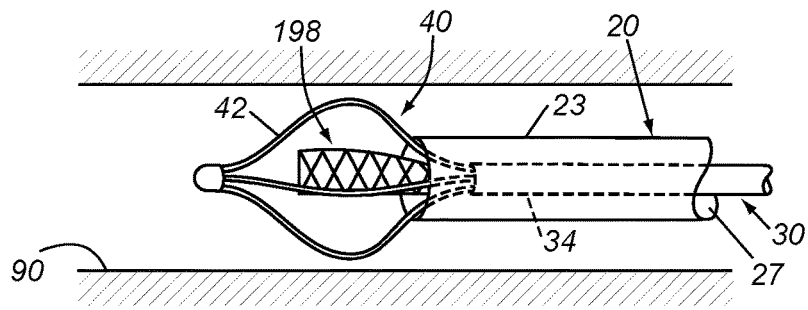

The expandable retrieval devices herein may be used in various medical procedures, e.g., including retrieving and/or removing clot or other material within a body, e.g., as shown in FIGS. 9A-9C, positioning a guidewire, e.g., as shown in FIGS. 10A and 10B, guide wire snaring, e.g., as shown in FIG. 11, and/or snaring, capturing, and/or removing a stent or other prosthesis, e.g., as shown in FIGS. 12A and 12B. Generally, the apparatus 10 of FIGS. 1A and 1B (including any of the retrieval devices herein) may be used to perform a procedure within a patient's vasculature, e.g., within a blood vessel, aorto-venous fistula, tubular graft, xenograft, and/or other body lumen, although alternatively, the apparatus may be used to treat other locations within a patient's body.

For example, FIGS. 9A-9C illustrate an exemplary method for retrieving clot or other obstructive material 92 from a blood vessel or other body lumen 90 using the apparatus 10 shown in FIGS. 1A and 1B. Initially, as shown in FIG. 9A, the distal end 23 of the sheath 20 may be introduced into the vessel 90, e.g., from a percutaneous entry site (not shown) and advanced and/or otherwise manipulated to position the distal end 23 adjacent to and spaced apart from the clot 92 within the vessel 90. A guidewire 98 may be introduced through the lumen 27 of the sheath 20 and advanced from the distal end 23 into the vessel 90 and through the clot 92. Alternatively, the guidewire 98 may already be positioned within the vessel 90 and/or through the clot 92 and the sheath 20 may be introduced over the guidewire 98 into the vessel 90.

A retrieval device 24, such as that shown in FIGS. 1A and 1B (or any of the other embodiments herein), may be introduced into the sheath lumen 27 with the cage(s) 40 in the collapsed configuration and advanced through the sheath 20 into the vessel 90. Alternatively, the retrieval device 24 may be loaded into the sheath 20 outside the patient's body or may be integrated with the sheath 20 as a single device (not shown) and the sheath 20 and retrieval device 24 (again with the cage(s) 40 in the collapsed configuration) may be advanced over the guidewire 98 into the vessel 90 together.

With the distal portion 26 of the retrieval device 24 within the sheath lumen 27 adjacent the distal end 23, the sheath 20 may be advanced into or through the clot 92, thereby directing the distal portion 26 into or through the clot 92, as shown in FIG. 9B. The sheath 20 may then be at least partially withdrawn while maintaining the retrieval device 24 substantially stationary to expose the distal portion 26, thereby deploying the cage(s) 40 within and/or distally beyond the clot 92, as shown in FIG. 9C. For example, in the embodiment shown in FIGS. 1A and 1B, the retrieval device 24 may be positioned such that the distal cage 40C is positioned distally beyond the clot 92 before deployment and the intermediate cage 40B is positioned within or proximal to the clot 92. In this alternative, the distal cage 40C may include filter material, similar to the retrieval device 24' shown in FIG. 3, to capture any clot that breaks loose during deployment and/or manipulation of the cage(s) 40.

The cage(s) 40 may resiliently expand upon deployment, e.g., until the struts 42 expand outwardly and contact the wall of the vessel 90. As explained above, as the struts 42 expand, the intermediate regions 42b may twist or rotate along their length, e.g., into the orientation shown in FIG. 2C, thereby increasing surface area contact with the clot 92 and/or otherwise enhancing engagement with the clot 92. The increased surface area may also provide a substantially atraumatic surface that contacts the vessel wall 90 to reduce the risk of damage. Optionally, as explained above, the struts 42 may include hooks or other engagement features (e.g., as shown in FIG. 4), which may enhance engaging or separating the clot material captured by the cage(s) 40.

The retrieval device 24 may then be at least partially withdrawn while maintaining the sheath 20 substantially stationary to direct the distal portion 26 (with clot material captured by the cage(s) 40) back into the sheath lumen 27, thereby collapsing the cage(s) 40 as they reenter the sheath lumen 27 and pull the clot material in with them. Optionally, a source of vacuum (not shown) may be coupled to the sheath 20, e.g., to a port (not shown) on the handle 28, such that the clot captured in the cage(s) 40 and pulled into the sheath lumen 27 may be aspirated from the sheath 20. In addition or alternatively, the retrieval device 24 may be pulled proximally through the sheath lumen 27 until the cage(s) 40 are removed from the proximal end 22 and the captured clot removed.

If desired, the sheath 20 and retrieval device 24 may be advanced and/or otherwise manipulated and the process of deploying and recapturing the cage(s) 40 repeated one or more times, as desired, until sufficient material 92 is removed from the vessel 90. One advantage of the retrieval device 24 is its ability to maintain guidewire position during clot removal, which may make re-crossing the clot 92 one or more times easier and safer. Once sufficient material 92 is removed, the retrieval device 24, sheath 20, and guidewire 98 may be removed from the patient's body.

Turning to FIGS. 10A and 10B, another method is shown for using a retrieval device 24 (which again may be any of the embodiments herein) to precisely position a guidewire 98 within a vessel 90, e.g., substantially centered within the vessel 90, as shown in FIG. 10A, or immediately adjacent the vessel wall 90, as shown in FIG. 10B. Initially, a distal end of the guidewire 98 may be introduced into the vessel 90 proximal to clot or other obstructive material 92 therein. With reference to the embodiment shown in FIG. 10A, the retrieval device 24 (such as that shown in FIGS. 1A and 1B but with only a single cage 40) may be loaded into a sheath (not shown), and the retrieval device 24 with the cage 40 in the collapsed configuration may be advanced into the vessel 90 over the guidewire 98, e.g., similar to the previous method (e.g., advancing the sheath and retrieval device 24 simultaneously or sequentially).

The distal end 34 of the retrieval device 24 may be positioned at the desired location, e.g., proximal to the clot 92 and then the cage 40 may be deployed, e.g., by at least partially withdrawing the sheath, thereby allowing the cage 40 to expand within the vessel 90 adjacent the clot 92. In the embodiment shown in FIG. 10B, expansion of the cage 140E within the vessel 90 positions the distal end 134 of the retrieval device 124E eccentrically within the vessel 90, e.g., adjacent the vessel wall 90. Thus, when a guidewire 98 is advanced from the retrieval device 124E through the lumen 136E, the guidewire 98 may enter and pass through the clot 92 immediately adjacent the vessel wall 90.

Alternatively, in the embodiment shown in FIG. 10A, expansion of the cage 40 within the vessel 90 substantially centers the distal end 34 within the vessel 90, thereby also substantially centering the distal end of the guidewire 98 within the vessel 90. The guidewire 98 may then be advanced into and through the clot 92 at the desired location within the vessel 90 and directed to its final location, e.g., where a procedure is to be performed. The retrieval device 24 may then be withdrawn back into the sheath 20 and removed entirely from the patient's body. One or more instruments (not shown) may then be advanced over the guidewire 98 to perform a procedure at the desired location. Thus, one of the advantages of the retrieval devices 24, 124E shown in FIGS. 10A and 10B are their ability to position the guidewire 98 at a desired location within the vessel lumen 90, e.g., centered (FIG. 10A) or offset (FIG. 10B), hence providing directional as well as axial support to the guidewire 98 and/or enabling the guidewire 98 to seek a path through a totally or partially occluded vessel segment.

Turning to FIG. 11, another exemplary method is shown in which a retrieval device 24 (e.g., the embodiment shown in FIGS. 1A and 1B with a single cage 40 and/or any other embodiment herein) is used to snare a guidewire 98 previously positioned within a blood vessel or other body lumen 90 from a different direction. For example, the retrieval device 24 may be loaded in a sheath 20 and/or advanced over another guidewire (not shown), similar to other methods herein, and advanced into the vessel 90 adjacent the distal end of the guidewire 98, which has been positioned within the vessel 90 from the opposite direction, as shown. In one embodiment, the sheath 20 and retrieval device 24 may be advanced simultaneously with the cage 40 being maintained in the collapsed configuration until positioned within the vessel 90. The sheath 20 may then be partially withdrawn to deploy and expand the cage 40 adjacent the guidewire 98 or with the cage 40 overlapping the end of the guidewire 98.

With the cage 40 expanded within the vessel 90, the retrieval device 24 may be advanced, rotated, and/or otherwise manipulated to capture the end of the guidewire 98 within the struts 42 of the cage 40. The sheath 20 may then be advanced to compress the cage 40 back towards the collapsed configuration, thereby snaring the end of the guidewire 98 within the compressed cage 40 in the sheath lumen 27. The sheath 20 and retrieval device 24 may then be withdrawn to pull the guidewire 98 back along the path used to introduce the sheath 20 and retrieval device 24 into the vessel 90. For example, the guidewire 98 may be directed back to the entry site used to introduce the sheath 20 and retrieval device such that both ends of the guidewire 98 are disposed outside the patient's body (not shown) or the end of the guidewire 98 may be released within another location, e.g., by redeploying the cage 40.

One advantage of using the retrieval device 24 in such a method is the ability to expand within a total artery occlusion, enabling snaring and pulling guidewires that are partially passed through the occlusion. This method may facilitate setting up a single guidewire that crosses the entire length of a long totally occluded artery.

Turning to FIGS. 12A and 12B, another exemplary method is shown for using a retrieval device 24 to snare or otherwise capture an undeployed stent, prosthesis, or other medical device 198, e.g., dislodged or otherwise released within a blood vessel or other body lumen 90. Similar to other methods herein, the retrieval device 24 may be loaded into a sheath 20 and introduced into the vessel 90, e.g., simultaneously or sequentially and/or over a guidewire (not shown). The sheath 20 and retrieval device 24 may be positioned within the vessel 90 such that the prosthesis 198 is aligned adjacent the cage 40 as shown (or between two cages on the retrieval device 24, not shown).

The cage(s) 40 may then be deployed from the sheath 20, e.g., by withdrawing the sheath 20, and the expanded cage(s) 40 may be rotated, advanced, retracted, and/or otherwise manipulated to capture the prosthesis 198, e.g., within the cage 40 as shown in FIG. 12A. The sheath 20 may then be advanced to captured and compress the cage 40, thereby compressing the prosthesis 198 and capturing the prosthesis 198 within the sheath lumen 27. The sheath 20 and retrieval device 24 may then be withdrawn to remove the prosthesis 198 from the patient's body. One advantage of this method is the ability to compress the prosthesis 198 during the retrieval process, which may allow lower profile guide sheaths to be used to remove the prosthesis than conventional methods.

The foregoing disclosure of the exemplary embodiments has been presented for purposes of illustration and description. It is not intended to be exhaustive or to limit the invention to the precise forms disclosed. Many variations and modifications of the embodiments described herein will be apparent to one of ordinary skill in the art in light of the above disclosure.

Further, in describing representative embodiments, the specification may have presented the method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

I claim:

1. A method for capturing material within a body lumen of a patient's body, comprising:
  introducing a distal end of a retrieval device into the body lumen with struts of an expandable cage thereon in a collapsed configuration;
  positioning the expandable cage adjacent material within the body lumen;
  expanding the expandable cage to an expanded configuration, thereby causing at least intermediate regions of the struts of the expandable cage to twist along their lengths to enhance engagement with the material within the body lumen;
  compressing the expandable cage back towards the collapsed configuration to capture the material; and
  removing the expandable cage in the collapsed configuration from the body lumen,
  wherein the struts having radial surfaces extending in a radial direction relative to a longitudinal axis of the expandable cage and outer circumferential surfaces in the collapsed configuration, and wherein the intermediate regions of the struts twist when expanded to the expanded configuration such that the radial surfaces become oriented substantially circumferentially and the outer surfaces become oriented substantially radially, and
  wherein the radial surface defines a thickness in the radial direction and the outer surface defines a maximum width in the circumferential direction that is smaller than the thickness.

2. The method of claim 1, wherein the material comprises a clot.

3. The method of claim 1, wherein the material comprises a prosthesis.

4. The method of claim 1, wherein the body lumen comprises one of a blood vessel, an aorto-venous fistula, and a tubular graft.

5. The method of claim 1, wherein introducing the distal end of the retrieval device comprises positioning the distal end of the retrieval device within a tubular sheath, the tubular sheath constraining the expandable cage in the collapsed configuration.

6. The method of claim 5, wherein expanding the expandable cage to an expanded configuration comprises deploying the expandable cage from the tubular sheath, whereupon the struts resiliently expand to the expanded configuration.

7. The method of claim 6, wherein compressing the expandable cage back towards the collapsed configuration comprises directing the expandable cage back into the tubular sheath.

8. A method for positioning a guidewire within a body lumen of a patient's body, comprising:
   introducing a distal end of an elongate member into the body lumen with struts of an expandable cage thereon in a collapsed configuration;
   positioning the expandable cage adjacent material within the body lumen;
   expanding the expandable cage to an expanded configuration, thereby causing at least intermediate regions of the struts of the expandable cage to twist along their lengths within the body lumen, the expandable cage aligning an outlet of a lumen on the distal end at a desired radial location within the body lumen; and
   advancing a distal end of a guidewire from the outlet into the body lumen into the material.

9. The method of claim 8, wherein the desired radial location is substantially centered within the body lumen.

10. The method of claim 8, wherein the desired radial location is offset from a center of the body lumen adjacent a wall of the body lumen.

11. The method of claim 8, further comprising compressing the expandable cage back towards the collapsed configuration after advancing the distal end of the guidewire.

12. The method of claim 11, further comprising removing the expandable cage in the collapsed configuration from the body lumen.

13. The method of claim 8, wherein the material comprises a clot.

\* \* \* \* \*